US009675311B2

(12) United States Patent
Von Berg et al.

(10) Patent No.: US 9,675,311 B2
(45) Date of Patent: Jun. 13, 2017

(54) FOLLOW UP IMAGE ACQUISITION PLANNING AND/OR POST PROCESSING

(75) Inventors: Jens Von Berg, Hamburg (DE); Julien Senegas, Hamburg (DE); Luna Fahoum, Nazareth (IL); Shlomo Gotman, Haifa (IL); Torbjorn Vik, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 549 days.

(21) Appl. No.: 14/126,276

(22) PCT Filed: Jun. 28, 2012

(86) PCT No.: PCT/IB2012/053296
§ 371 (c)(1),
(2), (4) Date: Dec. 13, 2013

(87) PCT Pub. No.: WO2013/005146
PCT Pub. Date: Jan. 10, 2013

(65) Prior Publication Data

US 2014/0198964 A1 Jul. 17, 2014

Related U.S. Application Data

(60) Provisional application No. 61/504,840, filed on Jul. 6, 2011.

(51) Int. Cl.
*G06K 9/00* (2006.01)
*A61B 6/00* (2006.01)
(Continued)

(52) U.S. Cl.
CPC .............. *A61B 6/488* (2013.01); *A61B 6/032* (2013.01); *A61B 6/469* (2013.01); *A61B 6/545* (2013.01); *G06T 7/30* (2017.01)

(58) Field of Classification Search
None
See application file for complete search history.

(56) References Cited

U.S. PATENT DOCUMENTS 7,747,050 B2 6/2010 Lau et al.
2007/0003123 A1* 1/2007 Fu ........................ A61N 5/1049 382/131

(Continued)

FOREIGN PATENT DOCUMENTS

JP 69111191 6/1994
JP 10108073 4/1998

(Continued)

*Primary Examiner* — Manuchehr Rahmjoo

(57) ABSTRACT

A method includes planning a follow up three dimensional image acquisition of tissue of interest of a patient based on first and second two dimensional surview projection images, wherein the first two dimensional surview projection image was used to plan a previously performed baseline three dimensional image acquisition of the tissue of interest of the patient, wherein the first two dimensional surview projection image includes information corresponding to at least one region of interest identified in the first two dimensional surview projection image for the previously performed baseline three dimensional image acquisition, wherein the first two dimensional surview projection image includes information corresponding to a z-axis scanning extent identified in the first two dimensional surview projection image for the previously performed baseline three dimensional baseline image acquisition, and wherein the second two dimensional surview projection image was acquired for planning the follow up three dimensional image acquisition.

21 Claims, 3 Drawing Sheets

Perform surview 402
Plan acquisition Using surview, including Defining a region of interest(s) and scan extent 404
Perform acquisition based on the plan 406
Reconstruct acquired data 408
Process reconstructed data 410
Store processed reconstructed data and surview 412
Perform subsequent surview 414
Retrieve stored surview 416
Register retrieved and subsequent surviews 418
Plan subsequent acquisition using registered subsequent surview, including transferring the region of interest(s) and scan extent to the subsequent surview 420
Perform subsequent acquisition based on the subsequent plan 422
Reconstruct acquired data 424
Retrieve stored processed reconstructed data 426
Register retrieved and subsequent reconstructed data, including transferring the ROIs 428
Process registered reconstructed images 430
Compare follow up and baseline images 432

(51) Int. Cl.
*A61B 6/03* (2006.01)
*G06T 7/30* (2017.01)

(56) References Cited

U.S. PATENT DOCUMENTS

| | | | | |
|---|---|---|---|---|
| 2007/0025524 | A1* | 2/2007 | Yue | A61N 5/1049 378/205 |
| 2007/0242865 | A1 | 10/2007 | Fenchel | |
| 2008/0159611 | A1 | 7/2008 | Tao et al. | |
| 2008/0317317 | A1* | 12/2008 | Shekhar | G06T 3/0081 382/131 |
| 2009/0080746 | A1 | 3/2009 | Xu et al. | |
| 2009/0147909 | A1 | 6/2009 | Yoda et al. | |
| 2012/0033869 | A1* | 2/2012 | Carlsen | G01R 33/56366 382/131 |
| 2012/0230563 | A1* | 9/2012 | Vik | A61B 6/032 382/128 |

FOREIGN PATENT DOCUMENTS

| | | |
|---|---|---|
| JP | 2003310586 | 11/2003 |
| JP | 2005012248 | 1/2005 |
| JP | 2008012171 | 1/2008 |
| WO | 2006056912 A1 | 6/2006 |
| WO | 2011058461 A1 | 5/2011 |

* cited by examiner

FOLLOW UP IMAGE ACQUISITION PLANNING AND/OR POST PROCESSING

CROSS-REFERENCE TO PRIOR APPLICATIONS

This application is the U.S. National Phase application under 35 U.S.C. §371 of International Application No. PCT/IB2012/053296, filed on Jun. 28, 2012, which claims the benefit of U.S. Provisional Patent Application No. 61/504,840, filed on July 6, 2011. These applications are hereby incorporated by reference herein.

FIELD OF THE INVENTION

The following generally relates to generating a follow up image acquisition plan and/or post processing of the data generated by the follow up image acquisition and is described with particular application to computed tomography (CT); however, the following is also amenable to other imaging modalities.

BACKGROUND OF THE INVENTION

A CT scanner includes an x-ray tube supported by a rotating gantry, which is rotatably affixed to a stationary gantry. The x-ray tube emits radiation that traverses an examination region and a portion of a patient therein (which attenuates the radiation as a function of the radiodensity of the patient). A subject support supports the patient and is configured to position the patient in the examination region for scanning. A detector array disposed across the examination region, opposite the x-ray tube, detects radiation traversing the examination region and produces projection data indicative of the detected radiation. The projection data can be reconstructed to generate three dimensional (3D) volumetric image data indicative of the portion of the patient.

For a CT acquisition (e.g. axial or helical), generally, a surview is first performed. The surview is acquired with the rotating gantry at a static position (not rotating) and with the subject support moving in the z direction through the examination region. The resulting data is a two dimensional (2D) projection image of the scanned portion of the patient. The 2D projection image is used to generate a plan for the CT acquisition, including identifying tissue of interest to be scanned during the CT acquisition and the z-axis extent of the patient (i.e., zmin and zmax) of the CT acquisition based on the tissue of interest. The extent is typically determined by the technician at the console on the 2D projection image by positioning and overlaying a region of interest (ROI) box that covers the tissue of interest.

Once planned, the CT acquisition can be performed. The acquired data is reconstructed, producing the 3D volumetric image data. However, typically, only a subset of the reconstructed data, for example, the portion corresponding particularly to the tissue of interest is further processed, for instance, optimized for visual inspection. This subset often includes slices with a thickness that is larger than the slices in the original reconstructed 3D volumetric image data. Furthermore, the subset may include images in multiple orientations (i.e., sagittal, transversal, and/or coronal). The subset and the surview is formatted in accordance with the Digital Imaging and Communications in Medicine (DICOM) standard and stored in a Picture Archiving and Communications System (PACS). The original reconstructed data may not be stored, e.g., due to its size.

CT acquisitions of the same tissue at different moments in time have been compared to obtain information about the tissue. For example, such acquisitions have been utilized to visually observe and/or quantify physical changes (e.g., growth or shrinkage) in the geometry of a tumor or other tissue over time. However, in order for the obtained information to be diagnostically useful, the acquisition settings should be similar. By way of example, if, for instance, the tumor diameter is measured in a baseline image in a given CT slice, the follow-up image should have geometry such that there is a corresponding slice with respect to the tumor position. Otherwise a difference in size of the tumor in the two data sets may be incorrectly estimated.

Typically, there is a standard operating procedure for a given examination type in a radiology department that determines where to place the ROI boxes. Unfortunately, the variability to be observed in real clinical data is high and does not allow an easy accurate comparison of baseline and follow-up images. Furthermore, it is extremely tedious and time consuming to manually position the ROI boxes so as to reproduce a baseline examination with sufficient accuracy. Therefore, there is an unresolved need for approaches for planning a follow up CT acquisition of tissue of interest where the tissue of interest in the resulting images is well suited for comparison with the tissue of interest in the baseline images.

SUMMARY OF THE INVENTION

Aspects of the present application address the above-referenced matters and others.

According to one aspect, a method includes planning a follow up three dimensional image acquisition of tissue of interest of a patient based on first and second two dimensional surview projection images, wherein the first two dimensional surview projection image was used to plan a previously performed baseline three dimensional image acquisition of the tissue of interest of the patient, wherein the first two dimensional surview projection image includes information corresponding to at least one region of interest identified in the first two dimensional surview projection image for the previously performed baseline three dimensional image acquisition, wherein the first two dimensional surview projection image includes information corresponding to a z-axis scanning extent identified in the first two dimensional surview projection image for the previously performed baseline three dimensional baseline image acquisition, and wherein the second two dimensional surview projection image was acquired for planning the follow up three dimensional image acquisition.

In another aspect, a system includes an acquisition planner configured to generate an acquisition plan for a follow up three dimensional image acquisition based on a first and second two dimensional surview projection images, wherein the first two dimensional surview projection image was used to plan a previously performed three dimensional image acquisition, and the second two dimensional surview projection image was acquired for planning the follow up three dimensional image acquisition.

In another aspect, computer readable medium embedded with computer executable instructions, which, when executed by a processor, causes the processor to: register a follow up surview 2D projection image performed for planning a subsequent three dimensional image acquisition with a baseline surview 2D projection image of a previously performed baseline a three dimensional image acquisition, transfer information corresponding to a region of interest identified in the baseline surview 2D projection image to the follow up surview 2D projection image, transfer information corresponding to a z-axis extent of the previously performed baseline a three dimensional image acquisition identified in the baseline surview 2D projection image to the follow up surview 2D projection image, and generating an acquisition plan for the subsequent three dimensional image acquisition based on the registered follow up surview 2D projection image with the transferred region of interest and z-axis extent, wherein the plan is used to perform the subsequent three dimensional image acquisition.

Still further aspects of the present invention will be appreciated to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following generally relates to replicating scan geometry of tissue of interest of a patient in a baseline image acquisition (e.g., position and orientation) for a follow up image acquisition of the same tissue of interest of the same patient. This allows for a better comparison of follow up images with baseline images as corresponding slices from both acquisitions cover the same anatomical extent. As used herein, "baseline" and "follow up" refer to acquisitions performed at different moments in time, wherein the "baseline" acquisition is performed before the "follow up" acquisition (or the "follow up" acquisition is performed subsequent to the "baseline" acquisition). However, the "baseline" acquisition is not necessarily the first acquisition, and the "follow up" acquisition is not necessarily the first acquisition performed after the "baseline" acquisition.

Figure 1:
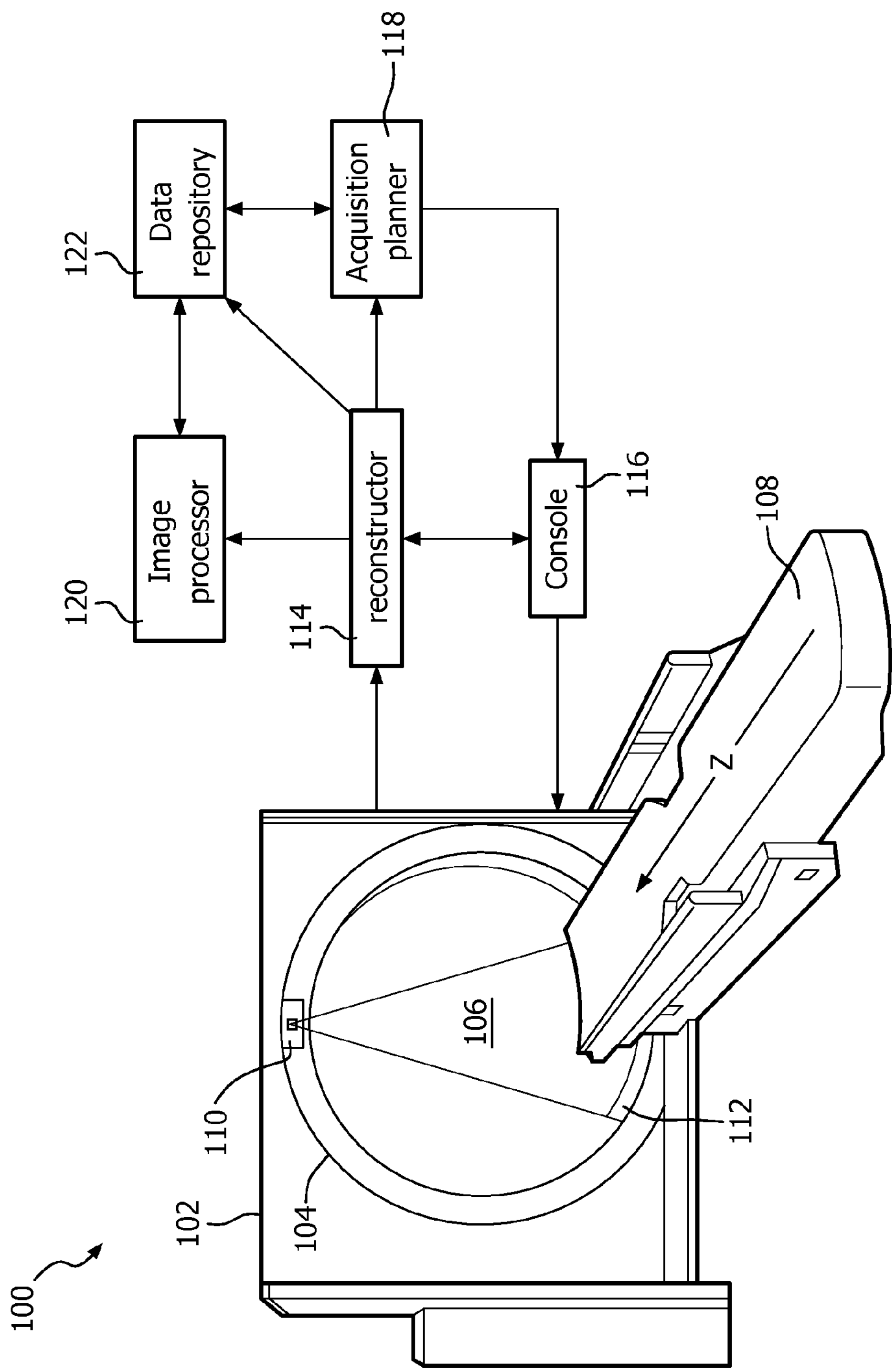
FIG. 1 schematically illustrates an example imaging system in connection with an acquisition planner and an image processor.

FIG. 1 illustrates an imaging system 100 such as a computed tomography (CT) scanner.

The imaging system 100 includes a stationary gantry 102 and a rotating gantry 104, which is rotatably supported by the stationary gantry 102. The rotating gantry 104 is configured to rotate around an examination region 106 about a longitudinal or z-axis for performing axial or helical acquisitions. The rotating gantry 104 is also configured to remain at a stationary location, for example, for performing one or more surviews. A support 108, such as a couch, supports a subject or object in the examination region 106 and can be used to position the subject or object with respect to x, y, and/or z axes before, during and/or after scanning.

A radiation source 110, such as an x-ray tube, is supported by the rotating gantry 104 and rotates with the rotating gantry 104, when the rotating gantry 104 is rotated, about the examination region 106. The radiation source 110 emits radiation that traverses the examination region 106. A radiation sensitive detector array 112 is located opposite the radiation source 110, across the examination region 106. The detector array 112 includes a one or two dimensional array of radiation sensitive detector elements that detect radiation traversing the examination region 106 and generate projection data indicative thereof.

A reconstructor 114 reconstructs the projection data and generates two dimensional (2D) and/or three dimensional (3D) volumetric image data indicative of the examination region 106 and a portion of an object or subject therein. The resulting volumetric image data can be processed by an image processor or the like to generate one or more images. A general purpose computing system serves as an operator console 116, and includes an output device such as a display and an input device such as a keyboard, mouse, and/or the like. Software resident on the console 116 allows the operator to control the operation of the system 100, for example, allowing the operator to initiate scanning, etc.

An acquisition planner 118 facilitates generating acquisition plans that are conveyed to the console 116 to be implemented by the scanner 100. As described in greater detail below, in one instance, the acquisition planner 118 generates a plan for a follow up (or subsequent) acquisition of tissue of interest of a patient based on a baseline surview(s) (e.g., generated by the scanner 100) used to plan a baseline acquisition of the tissue of interest of the patient and a subsequent surview(s) (e.g., generated by the scanner 100) for planning the follow up acquisition. This allows for automatically replicating the scan geometry of the baseline acquisition of a patient with respect to the tissue of interest position and orientation. Note that the baseline and follow-up acquisitions can be performed with different CT scanners.

An image processor 120 facilitates processing reconstructed image data, such as data from the reconstructor 114. As described in greater detail below, in one instance, the image processor 120 matches thin slices (e.g. 0.5 mm thick) from reconstructed image data from the follow up acquisition (e.g., produced by the reconstructor 114) that correspond to slices in a baseline image set, which may include the entire reconstructed image data for the baseline acquisition (e.g., produced by the reconstructor 114) with thin slices that may or may not have the same slice thickness as the follow up acquisition thin slices or a subset thereof that have been processed and include thicker slices (e.g., produced by the image processor 120). This matching allows a better comparison of the tissue of interest in the two acquisitions relative to a configuration in which the image processor 120 is not employed.

The acquisition planner 118 and/or the image processor 120 can be part of a computing system such as a computer. In this instance, the acquisition planner 118 and/or the image processor 120 can be located local to or remote from the scanner 100. In another instance, the acquisition planner 118 and/or the image processor 120 is part of the console 116. In either instance, the acquisition planner 118 and/or the image processor 120 can be implemented via one or more processors that execute one or more computer readable instructions embedded on computer readable medium such as physical memory. Additionally or alternatively, the one or more processors execute one or more computer readable instructions carried by a signal or carrier wave.

A data repository 122 is configured to store electronically formatted data, including, but not limited to, surviews (e.g., generated by the scanner 100), reconstructed image data (e.g., generated by the scanner 100), processed image data (e.g., generated by the image processor 120), and/or other information. This data can be used by the acquisition planner 118 to facilitate generating acquisition plans and/or the image processor 120 to facilitate processing reconstructed data. The data repository 122 can include one or more storage components such as a PACS, a radiology information system (RIS), a hospital information system (HIS), an electronic medical record (EMR), a database, a server, and/or other repository.

Figure 2:
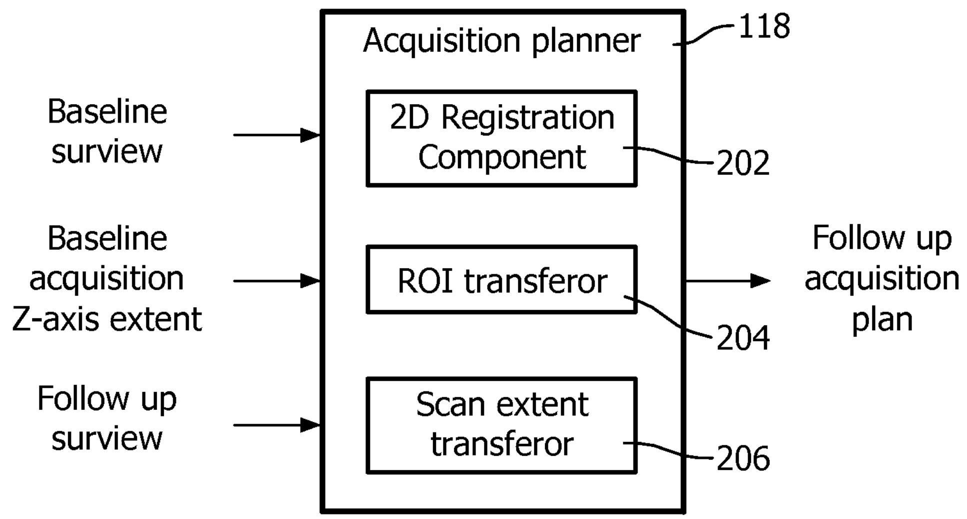
FIG. 2 schematically illustrates an example of the acquisition planner.

FIG. 2 schematically illustrates an example of the acquisition planner 118.

In this example, the acquisition planner 118 is discussed in connection with planning a follow up acquisition of the same tissue of interest of the same patient. In this context, the acquisition planner 118 utilizes a baseline surview(s) (e.g., generated by the scanner 100 and stored in the data repository 122), including the ROI box(s) and z-axis extent, and a follow up surview (e.g., generated by the scanner 100). It is to be understood that the acquisition planner 118 can also be utilized to plan the baseline acquisition based on the baseline surview and that this will not be discussed below.

The illustrated acquisition planner 118 includes a two dimensional (2D) registration component 202, which registers the baseline surview(s) and the follow up surview(s). In one instance, this includes rigidly or elastically registering all or a subset of the structure represented in both to the surviews. Any known or other 2D registration algorithm can be employed. An example of a suitable registration includes an image pixel intensity based registration. A global or locally restricted similarity measure between both images can be maximized by variation of the geometric parameters (e.g., changing position and orientation of one image in rigid registration).

The illustrated acquisition planner 118 further includes a region of interest (ROI) transferor 204 that transfers ROIs of the baseline surview(s) to the follow up surview(s) that has been registered with the baseline surview(s). The illustrated acquisition planner 118 further includes a scan extent transferor 206 that transfers the scan extent (zmin and zmax) of the baseline surview(s) to the subsequent surview(s) that has been registered with the baseline surview(s).

Figure 3:
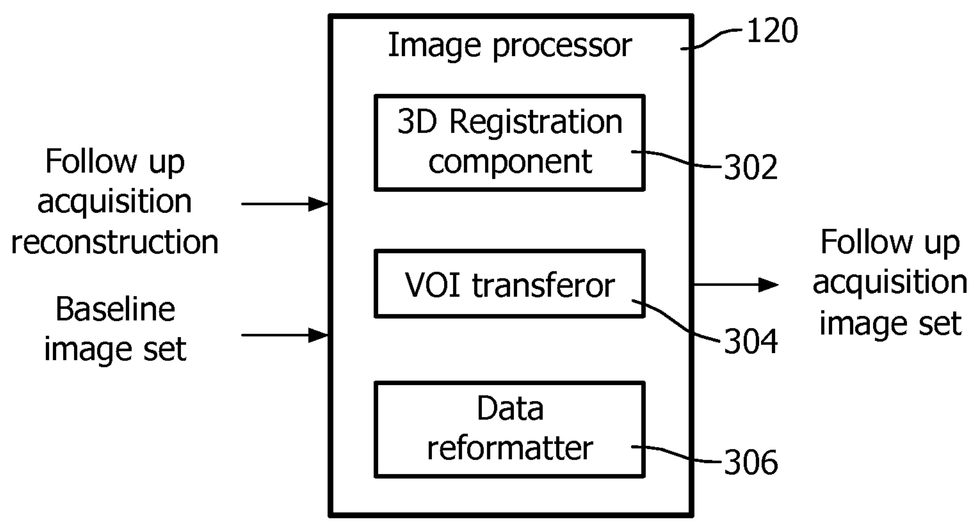
FIG. 3 schematically illustrates an example of the image processor.

FIG. 3 schematically illustrates an example of the image processor 120.

In this example, the image processor 120 is discussed in connection with matching images of the follow up reconstruction with corresponding images of the baseline image set. It is to be understood that the image processor 120 can also be utilized to process the baseline acquisition.

The image processor 120 includes a three dimensional (3D) elastic or rigid registration component 302, which registers the baseline images and the subsequent reconstructed thin slice images. Any known or other 3D registration algorithm can be employed. An example of a suitable registration includes an image pixel intensity based registration. A global or locally restricted similarity measure between both images can be maximized by variation of the geometric parameters (e.g., changing position and orientation of one image in rigid registration).

In one instance, the registration includes registering the baseline reconstructed images and/or the subset of processed images derived from the baseline reconstructed images with the reconstructed images of the follow up acquisition. This registration allows for refining the position of the follow up ROI(s), thereby optimizing alignment of the ROI(s) in the reconstructed images of the two acquisitions.

A data reformattor 306 reformats the thin slice reconstructed images of the follow up acquisition based on the registration transformation. This may include creating a set of images from the set of registered thin slice image using image processing approaches such as multi-planar reconstruction (MPR) and/or other image processing approaches. In one instance, the resulting image dataset includes a three dimensional image dataset that substantially matches the three dimensional subset of reconstructed images derived from the baseline acquisition. The resulting image dataset can be visually presented via a display monitor, stored, conveyed to one or more or devices, further processed, filmed, etc.

Generally, the estimation from the registration of the baseline and follow up surviews is used to guide this 3D registration. The 3D search space is already strongly limited by it, especially in the in-plane orientations of the surview. This way, the capture range problem of the 3D registration is already limited. This increases robustness and speeds up computation. In case a dual projection surview is available (two orthogonal projections of the patient), these restrictions can be made even stronger.

The image processor 120 also includes a volume of interest (VOI) transferor 304 that transfers VOIs from the baseline image set to the follow up image set.

Figure 4:
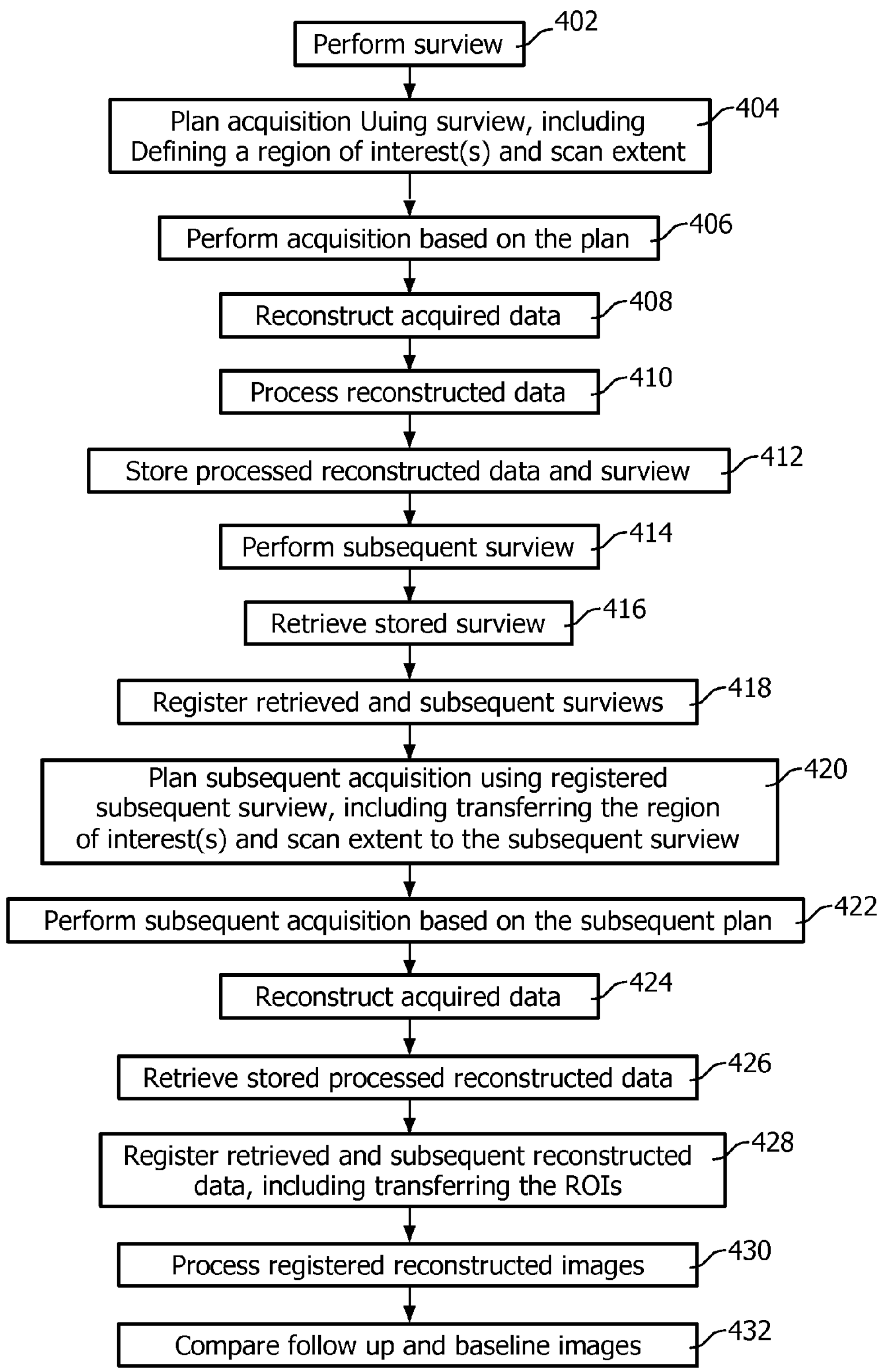
FIG. 4 illustrates an example method for performing CT scans.

FIG. 4 schematically illustrates an example method for performing CT scans.

It is to be appreciated that the ordering of the below acts is for explanatory purposes and not limiting. As such, other orderings are also contemplated herein. In addition, one or more of the acts may be omitted and/or one or more other acts may be included.

At 402, at least one surview is performed for a patient to be scanned. Where there are multiple surviews, the surviews can be performed with the radiation source 110 located at different angular positions.

At 404, an acquisition plan is created, based on the surview(s), for scanning tissue of interest of the patient. This includes defining one or more ROIs for tissue of interest and a z-axis scan extent on the surview.

At 406, an acquisition is performed based on the plan.

At 408, the acquired data is reconstructed, creating a plurality of thin slices.

At 410, the reconstructed data is processed. In one instance, this includes creating a subset of images for the tissue of interest, where the images have a greater slice thickness relative to the reconstructed thins slices and includes at least one user identified volume of interest (VOI).

At 412, the surview with the ROIs and the z-axis extent and the subset of images are stored. Optionally, the original reconstructed slices are also stored.

At 414, at least one follow up surview for planning a follow-up acquisition of the tissue is performed.

At 416, the one or more stored surviews, including the one or more ROIs and the z-axis extent, are retrieved. This data can be pre-fetched or obtained when needed.

At 418, the one or more follow up surviews are registered with the one or more retrieved surviews, including transferring the ROIs and z-axis extent of the retrieved surviews to the follow up surviews. In one instance, the registration is automatically performed without any user interaction. In another instance, the registration is performed under user interaction. The resulting registration can be accepted, modified or rejected.

At 420, a follow up acquisition plan is created based on the registered subsequent surview, including the registered ROIs and z-axis extent. In one instance, the plan is automatically created without any user interaction. In another instance, the plan is created under user interaction. The resulting plan can be accepted, modified or rejected.

At 422, a follow up acquisition is performed based on the follow up acquisition plan.

At 424, the acquired data is reconstructed, creating a plurality of thin slices.

At 426, the stored subset of reconstructed images is retrieved. Additionally or alternatively, the stored reconstructed data is retrieved.

At 428, the reconstructed thin slice images of the reconstructed data are registered with the retrieved subset of reconstructed images, including transferring the at least one VOI. The images in both sets cover the same tissue of interest, slice-by-slice.

At 430, the registered reconstructed images are processed. In one instance, this includes creating a subset of images for the tissue of interest.

At 432, the tissue of interest in the follow up processed images is compared with the tissue of interest in the baseline processed images. This may include visually and/or quantitatively comparing the tissue of interest of the two data sets.

Where another follow up acquisition is to be planned, one or more of acts 414 to 432 are repeated, using the initial surview, the first follow up surview, both of these surviews, and/or another surview.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

It is to be appreciated that the above can facilitate driving the acquisition and reconstruction of a follow-up exam such that the follow-up and baseline 3D images are substantially identical on a slice-by-slice basis (e.g. slice #38 of the baseline and follow-up datasets contain the same anatomical structures, with as less through-plane and in-plane translation/angulation as possible). By computing a transformation based on a thin-slice reconstruction of the follow-up exam (before the image with thicker slices is reconstructed), a MPR in the desired orientation can be computed directly, therefore reducing artifacts due to partial volume, relative to a configuration in which baseline and follow-up images with relatively thick slices are registered together, and the thick-slice follow-up image is reformatted to match the baseline image, which results in stronger partial-volume effect.

The above is discussed in terms of planning a CT acquisition based on CT surviews. However, it is to be appreciated the CT acquisition plans can additionally or alternatively be generated based on data from other imaging modalities. In addition, plans for other imaging modalities can be generated based on a CT surview and/or data generated based on other imaging modalities.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:

generating an acquisition plan for a follow up three dimensional image acquisition of tissue of interest of a patient by computer tomography (CT) acquisition based on a first two dimensional surview projection image registered with a second two dimensional surview projection image, wherein the first two dimensional surview projection image was used to plan a previously performed baseline three dimensional image acquisition of the tissue of interest of the patient, wherein the first two dimensional surview projection image includes information corresponding to at least one region of interest identified in the first two dimensional surview projection image for the previously performed baseline three dimensional image acquisition, wherein the first two dimensional surview projection image includes information corresponding to a z-axis scanning extent identified in the first two dimensional surview projection image for the previously performed baseline three dimensional baseline image acquisition, and the information corresponding to the z-axis scanning extent includes a first position scanned and a last position scanned of the previously performed baseline three dimensional image acquisition, and wherein the second two dimensional surview projection image was acquired for planning the follow up three dimensional image acquisition, and wherein the z-axis scanning extent including the first position scanned and the last position scanned of the previously performed three dimensional image acquisition is transferred from the first two dimensional surview projection image to the second two dimensional surview projection image according to the registration.

2. The method of claim 1, further comprising:

registering the first and second two dimensional surview projection images, wherein the planning of the follow up three dimensional image acquisition is based on the registered first and second two dimensional surview projection images and the registration includes anatomical structures of the tissues of interest represented in the registered first and second two dimensional surview projection images.

3. The method of claim 2, the registering, comprising:

using an elastic image registration algorithm to register first and second two dimensional surview projection images.

4. The method of claim 2, the registering, comprising:

transferring the information corresponding to the at least one region of interest and the information corresponding to the z-axis scanning extent that includes the first position scanned and the last position scanned from the first two dimensional surview projection image to the second two dimensional surview projection image according to the registration.

5. The method of claim 2, wherein the registering of the first and second two dimensional surview projection images is performed automatically without user interaction.

6. The method of claim 2, further comprising:

performing the follow up three dimensional image acquisition based on the registered second two dimensional surview projection image with the transferred information; and wherein the acquisition plan includes replicating scan geometry of the tissue of interest with respect to position and orientation.

7. The method of claim 6, the registering of the slice images, comprising:

transferring information corresponding to a volume of interest identified in the subset of images from the subset to the registered plurality of thin slice images.

8. The method of claim 7, further comprising:

reformatting the plurality of thin slice images, producing a three dimensional image dataset that substantially matches anatomy in each of the subset of images corresponding to the previously performed three dimensional baseline image acquisition.

9. The method of claim 1, further comprising:

reconstructing data acquired during the follow up three dimensional image acquisition, generating a plurality of slice images of the follow up three dimensional image acquisition; and registering the slice images of the follow-up three dimensional image acquisition with a subset of images corresponding to the previously performed three dimensional baseline image acquisition slice-by-slice.

10. The method of claim 9, wherein the subset of images is derived from a set of slice images generated from the previously performed three dimensional baseline image acquisition.

11. The method of claim 9, wherein the subset of images have slice thicknesses greater than the slice images generated from the previously performed three dimensional baseline image acquisition.

12. The method of claim 1, wherein the first two dimensional surview projection image, the second two dimensional surview projection image and the previously performed three dimensional imaging acquisition include image data generated from a computed tomography scanner.

13. A system, comprising:

an acquisition planner which comprises one or more processors configured to generate an acquisition plan for a follow up three dimensional image acquisition of a patient by a computed tomography acquisition based on a first two dimensional surview projection image registered with a second two dimensional surview projection image, wherein the first two dimensional surview projection image was used to plan a previously performed three dimensional image acquisition, wherein the first two dimensional surview projection image includes information corresponding to a z-axis scanning extent identified in the first two dimensional surview projection image for the previously performed three dimensional image acquisition and the information corresponding to the z-axis scanning extent includes a first position scanned and a last position scanned of the previously performed three dimensional image acquisition, wherein the second two dimensional surview projection image was acquired for planning the follow up three dimensional image acquisition, wherein the acquisition planner includes a scan extent transferor configured to transfer the z-axis scanning extent including the first position scanned and the last position scanned of the previously performed three dimensional image acquisition from the first two dimensional surview projection image to the second two dimensional surview projection image.

14. The system of claim 13, the acquisition planner, comprising:

a 2D registration component that registers the first and second two dimensional surview projection images and the registration includes anatomical structures of the tissue of interest represented in the registered first and second two dimensional surview projection images.

15. The system of claim 14, the acquisition planner, further comprising:

a region of interest transferor that transfers information corresponding to at least one region of interest identified in the first two dimensional surview projection image to the second two dimensional surview projection image.

16. The system of claim 13, further comprising:

an image processor that matches thin slice images of the follow up three dimensional image acquisition with a subset of thicker slice images derived from the thin slice images of the previously performed three dimensional image acquisition.

17. The system of claim 16, the image processor, comprising:

a 3D registration component configured to register the thin slice images and the thicker slice images.

18. The system of claim 17, the image processor, comprising:

a volume of interest transferor configured to transfer information corresponding to a volume of interest identified in the subset of images to the registered plurality of thin slice images.

19. The system of claim 18, further comprising:

a data reformattor comprising the one or more processors configured to reformat the registered plurality of thin slice images based on the registration transformation, producing a three dimensional set of images that substantially matches anatomy in the thicker slice images of the previously performed three dimensional image acquisition.

20. The system according to claim 13, wherein the first two dimensional surview projection image, the second two dimensional surview projection image and the previously performed three dimensional image acquisition include data generated from a computed tomography scanner.

21. A non-transitory computer readable medium embedded with computer executable instructions, which, when executed by a processor, causes the processor to:

register a follow up surview 2D projection image performed for planning a subsequent three dimensional image acquisition with a baseline surview 2D projection image of a previously performed baseline a three dimensional image acquisition of a patient with a computed tomography acquisition;

transfer information corresponding to a region of interest identified in the baseline surview 2D projection image to the follow up surview 2D projection image; wherein the transfer information corresponds to a z-axis extent including a first position scanned and a last positioned scanned of the previously performed baseline a three dimensional image acquisition identified in the baseline surview 2D projection image to the follow up surview 2D projection image; and generating an acquisition plan for the subsequent three dimensional image acquisition based on the registered follow up surview 2D projection image with the transferred region of interest and z-axis extent, wherein the plan is used to perform the subsequent three dimensional image acquisition.

* * * * *